United States Patent [19]

Kurihara et al.

[11] Patent Number: 5,178,900

[45] Date of Patent: Jan. 12, 1993

[54] METHOD FOR STABILIZING TASTE-MODIFIER

[75] Inventors: Yoshie Kurihara, 4-7, Okuzawa 7-chome, Setagaya-ku, Tokyo, Japan, 125; Hiroshige Kohno, Tokyo, Japan; Masaaki Kato, Tokyo, Japan; Kenji Ikeda, Tokyo, Japan; Masako Miyake, Tokyo, Japan

[73] Assignees: Yoshie Kurihara; Asahi Denka Kogyo Kabushiki Kaisha, both of Tokyo, Japan

[21] Appl. No.: 598,799

[22] Filed: Oct. 16, 1990

Related U.S. Application Data

[63] Continuation of Ser. No. 362,871, Jun. 7, 1989, abandoned.

[30] Foreign Application Priority Data

Jun. 21, 1988 [JP] Japan ............................ 63-153143
Nov. 2, 1988 [JP] Japan ............................ 63-277717
Nov. 11, 1988 [JP] Japan ............................ 63-285473

[51] Int. Cl.$^5$ ............................................. A23L 1/221
[52] U.S. Cl. ................................... 426/655; 426/615; 426/638; 426/650; 426/534
[58] Field of Search ............... 426/615, 638, 650, 534, 426/655

[56] References Cited

U.S. PATENT DOCUMENTS 4,160,860  7/1979  Pegel .................................. 426/655
4,830,862  5/1989  Braun et al. ........................ 426/599

OTHER PUBLICATIONS

Dialog Data Base, File 50: CAB Abstracts 1984–1989, Accession No. 0862549, Abstracting "A Review of Hypoxidaceae in India" (1988).

*Primary Examiner*—Joseph Golian
*Attorney, Agent, or Firm*—Frishauf, Holtz, Goodman & Woodward

[57] ABSTRACT

A method for stabilizing a taste-modifier comprising fresh *Curculigo latifolia* fruits, dried fruits thereof or a curuculin-containing material obtained therefrom which comprises heating said taste-modifier to 50° to 90° C.; or subjecting said taste-modifier to ultrahigh-temperature short-time pasteurization at 110° to 150° C. for two seconds to two minutes; is disclosed. Curuculin is a coined name for protein extracted from *C. latifolia*. Either of these methods enables the stable preservation of said taste-modifier, which is in the form of a crude product or an aqueous solution, for prolonged period of time.

4 Claims, No Drawings

METHOD FOR STABILIZING TASTE-MODIFIER

This application is a continuation of application Ser. No. 07/362,871, filed Jun. 7, 1989, now abandoned.

BACKGROUND OF THE INVENTION

1. Field of the Invention

This invention relates to a method for stabilizing a taste-modifier which comprises fresh *Curculigo latifolia* fruits, dried fruits thereof or a curuculin, a name coined by one of the present inventors containing material obtained therefrom.

2. Description of the Prior Art

Known taste-modifiers which affect the receptor membranes on the tongue in such a manner as to modify the taste of a food, include those which remove the sweetness of a sweet food in the mouth, for example, gymnemic acid contained in *Gymnema sylvestre* leaves and ziziphine contained in *Ziziphus jujuba* leaves; and those which convert the sourness of a sour food into sweetness in the mouth, for example, miraculin contained in *Synsepulm dulcificum* fruits.

Although miraculin has the abovementioned effect, it is not put into practical use as a taste-modifier because of its poor stability.

The present inventors have found that a sour material or water taken after eating *Curculigo latifolia* fruits would taste sweet. Thus they have attempted to identify the sweetness-inducer. As a result, they have found that a specific protein contained in *Curculigo latifolia* fruits is the aimed sweetness-inducer (cf. Japanese Patent Application No. 153143/1988). This protein is named curuculin. In order to utilize this curuculin as a taste-modifier on a commercial scale, it is required to obtain crude curuculin in a stable form from *Curculigo latifolia* fruits as efficiently as possible.

Pure ciruculin may be obtained by washing fresh *Curculigo latifolia* fruits or dried fruits thereof with water, extracting from them with an aqueous solution of a salt and purifying the extract by ion-exchange chromatography with the use of CM-Sepharose and HPLC with the use of a gel column. Pure or almost pure curuculin would remain stable for a month or longer in the form of an aqueous solution at room temperature. However fresh *Curculigo latifolia* fruits, dried fruits thereof or crude curuculin, in particular, in the form of an aqueous solution, would have a poor stability upon storage since they are contaminated with proteases and bacteria contained in the *Curculigo latifolia* fruits.

SUMMARY OF THE INVENTION

It is an object of the present invention to provide a method for stabilizing a taste-modifier comprising a protein curculin in a state of a crude product or an aqueous solution for a prolonged period of time.

The present inventors have conducted extensive studies in order to achieve the above object. As a result, they have found that the protein curuculin is stable to heat and thus the taste-modification activity thereof would be never lowered when *Curculigo latifolia* fruits are heated in order to pasteurize the same as well as to inactivate proteases contained therein.

Accordingly the present invention, which has been completed based on the above finding, provides the following methods (1) and (2) for stabilizing a taste-modifier.

(1) A method for stabilizing a taste-modifier comprising fresh *Curculigo latifolia* fruits, dried fruits thereof or a curuculin-containing material obtained therefrom which comprises heating said taste-modifier to 50° to 90° C. (the first invention).

(2) A method for stabilizing a taste-modifier comprising fresh *Curculigo latifolia* fruits, dried fruits thereof or a curuculin-containing material obtained therefrom which comprises subjecting said taste-modifier to ultrahigh-temperature short-time pasteurization at 110° to 150° C. for two seconds to two minutes (the second invention).

According to the method for stabilizing a taste-modifier of the present invention, a taste-modifier comprising fresh *Curculigo latifolia* fruits, dried fruits thereof or a curuculin-containing material obtained therefrom can be pasteurized and proteases contained therein can be inactivated without lowering the taste-modification activity of the same. Thus the taste-modifier can be stably preserved for a prolonged period of time in the form of a crude product or an aqueous solution.

DETAILED DESCRIPTION OF THE INVENTION

Now the first invention will be described.

The taste-modifier comprising fresh *Curculigo latifolia* fruits, dried fruits thereof or a curuculin containing material obtained therefrom can be stabilized by heating to 50° to 90° C., preferably 60° to 80° C. Thus it can be pasteurized and proteases contained therein can be simultaneously inactivated.

The heating period may be five minutes or longer, preferably from five minutes to 24 hours. The necessary heating period would increase with a decrease in the heating temperature. For example, it is preferable to heat the taste-modifier to 50° C. for 30 minutes or longer, preferably 30 minutes to 24 hours; and to 90° C. for five minutes or longer, preferably 5 to 60 minutes.

When the heating temperature is lower than 50° C. the aimed pasteurization and inactivation effects can not be fully achieved. When it exceeds 90° C. on the other hand, the taste-modification effect of the taste-modifier might be lowered.

After the completion of the heating, the taste-modifier may be filled in a container or dried. It may be stabilized and dried with a hot air stream at 50° to 90° C.

Now the second invention will be described.

The second invention, which comprises subjecting the taste-modifier to ultrahigh-temperature short-time pasteurization at 110° to 150° C. for two seconds to two minutes, is preferred to the first one in order to stabilize the taste-modifier in the form of a solution or a fluid, since the pasteurization and the inactivation of the protease can be completely effected and the tate-modifier can be filled under aseptic conditions.

The ultrahigh-temperature short-time pasteurization may be carried out with the use of any device. As described above, the taste-modification activity of the taste-modifier might be lowered when heated at 90° C. or above for a long period. Thus the ultrahigh-temperature short-time pasteurization may be appropriately effected for two seconds to two minutes.

According to the present invention, the taste-modifier comprising fresh *Curculigo latifolia* fruits, dried fruits thereof or a citruculin-containing material obtained therefrom is heated to 50° to 90° C. (i.e., the first invention) or subjected to ultrahigh-temperature short-time pasteurization at 110° to 150° C. for two seconds to two minutes (i.e., the second invention) to thereby stabilize said taste-modifier. When the taste-modifier is in the form of a solution or a fluid, the second invention is preferred to the first one.

The methods (1) and (2) for stabilizing the taste-modifier of the present invention may be conducted at any stage in the purification of curuculin. In addition, these methods may be applied to the taste-modifier in any form, i.e., a dried matter, a solution or dispersion in water or a product containing the same.

The fresh *Curculigo latifolia* fruits or dried fruits thereof constituting the taste-modifier to be used in the present invention may be preferably free from peels and seeds, since no curuculin is contained in these parts.

The method for drying *Curculigo latifolia* fruits is not particularly restricted. Namely, sun-dried *Curculigo latifolia* fruits, hot air-dried ones and lyophilized ones such as lyophilized pulp may be used in the present invention.

The fresh *Curculigo latifolia* fruits or dried fruits thereof may be generally ground, milled or pasted prior to the use, though the form of the optionally dried *Curculigo latifolia* fruits is not particularly restricted.

Examples of the curuculin-containing material obtained from fresh *Curculigo latifolia* fruits or dried fruits thereof described above include curuculin extracted from fresh *Curculigo latifolia* fruits, dried fruits thereof or the residue obtained by appropriately treating the fresh *Curculigo latifolia* fruits or dried fruits thereof and removing a curuculin-free component therefrom. The concentration of the curuculin extracted from fresh *Curculigo latifolia* fruits or dried fruits thereof is not particularly restricted. Namely, either a highly pure curuculin or an extract containing a large amount of materials other than the curuculin may be used in the present invention. Further the extract may be mixed with other components.

The extraction of the curuculin is not particularly restricted. A preferable example thereof comprises extracting from fresh *Curculigo latifolia* fruits or dried fruits thereof with an aqueous solution of a salt at a concentration of at least 0.01M. Examples of the salt include chlorides such as sodium chloride, potassium chloride, calcium chloride, magnesium chloride and ammonium chloride; phosphates such as sodium phosphate, potassium phosphate, magnesium phosphate and ammonium phosphate; carbonates such as sodium carbonate, potassium carbonate, magnesium carbonate and ammonium carbonate; sulfates such as sodium sulfates, magnesium sulfate, calcium sulfate and ammonium sulfate; sulfites such as sodium sulfite, magnesium sulfite, calcium sulfite and ammonium sulfite; nitrates such as sodium nitrate and potassium nitrate; nitrites such as sodium nitrite and potassium nitrite; lactates such as sodium lactate and calcium lactate; alum; burnt alum; sodium acetate; pyrophosphates such as sodium pyrophosphate and potassium pyrophosphate; propionates such as sodium propionate and calcium propionate; sodium benzoate; sodium fumarate; and sodium polyacrylate.

A typical example of the extraction of curuculin with the aqueous solution of a salt may be carried in the following manner.

An aqueous solution of a salt such as sodium chloride is added to fresh *Curculigo latifolia* fruits or dried fruits thereof and the obtained mixture is homogenized followed by filtering and centrifuging. Since curuculin is contained in the water-insoluble part of *Curculigo latifolia* sarcocarp, it is preferable to homogenize the above mixture of the fresh *Curculigo latifolia* fruits or dried fruits thereof and water followed by thoroughly washing the mixture to thereby remove the water-soluble part and extracting from the residue with the above-mentioned salt solution so as to increase the purity of curuculin.

The concentration of the salt of the aqueous solution to be used for the extraction should exceed 0.01M. since curuculin can not be sufficiently extracted with a salt solution of a concentration lower than 0.01M. On the other hand, a salt solution of an excessively high concentration requires a prolonged period of time for desalting following the extraction. Thus the concentration of the salt solution preferably ranges from 0.1 to 1.0M. from the viewpoints of the extraction efficiency and the subsequent purification procedure.

The extract thus obtained with the use of the salt solution is then desalted and dried to thereby give a curuculin-containing material which is sufficiently available in practice. However the purity of curuculin can be further increased by purifying the above extract by ion exchange chromatography with the use of CM-Sepharose and HPLC with the use of a gel column followed by desalting and drying. Thus pure curuculin can be obtained. It is a matter of course that the curuculin purity may be further increased by various purification procedures other than those described above, for example, known protein purification procedures such as salting-out or solvent precipitation.

A typical example of the curuculin thus obtained is a protein having a molecular weight of approximately 12,500 dalton, an amino acid residue number of 97 and an iso-electric point of 7.1. This protein is present as a dimer of a molecular weight of approximately 26,000 dalton. The following Table 1 shows the amino acid composition of this protein. Thus it contains relatively large amounts of aspartic acid, leucine and glycine.

TABLE 1

| Amino acid composition | | |
|---|---|---|
| Amino acid | % by mol | No. of residues |
| Aspartic acid (Asp) | 17.3 | 17 |
| Threonine (Thr) | 6.4 | 6 |
| Serine (Ser) | 7.0 | 7 |
| Glutamic acid (Glu) | 7.2 | 7 |
| Proline (Pro) | 1.2 | 1 |
| Glycine (Gly) | 12.5 | 12 |
| Alanine (Ala) | 5.3 | 5 |
| Cystine (Half-cys) | — | — |
| Valine (Val) | 6.8 | 7 |
| Methionine (Met) | 0.4 | 1 |
| Isoleucine (Ile) | 4.2 | 4 |
| Leucine (Leu) | 14.5 | 14 |
| Tyrosine (Tyr) | 5.2 | 5 |
| Phenylalanine (Phe) | 1.3 | 1 |
| Lysine (Lys) | 2.7 | 3 |
| Histidine (His) | 2.4 | 2 |
| Arginine (Arg) | 5.5 | 5 |
| Total | | 97 |

To further illustrate the present invention, the following Examples are provided.

EXAMPLE 1

*Curculigo latifolia* fruits were washed with water and peels and seeds were removed therefrom. The residual sarcocarp was ground in a mortar.

Then the ground sarcocarp was dried with a hot air stream at 65° C. for 24 hours to thereby give a taste-modifier.

100 mg of the taste-modifier was kept in the mouth for one minutes and then expectorated. Subsequently a 0.02M aqueous solution of citric acid was kept in the mouth. Then the citric acid solution tasted sweet just like a sugar solution does.

This taste-modifier was introduced into an sterile Petri dish and allowed to stand at 37° C. for three months. Then it was subjected to the same sensory test as the one described above. As a result, it showed an intense sweetness similar to the above case.

EXAMPLE 2

50 ml of water was added to 10 g of *Curculigo latifolia* sarcocarp ground in the same manner as the one described above. Then the mixture was homogenized and centrifuged at 10,000 rpm for 30 minutes. After removing the supernatant, 50 ml of water was added to the residue and the obtained mixture was homogenized. Then it was heated to 70° C. for 20 minutes and centrifuged at 10,000 rpm for 30 minutes. After removing the supernatant, the residue was obtained.

This residue was dried under reduced pressure to thereby give a taste-modifier.

10 mg of this taste-modifier was kept in the mouth for a minutes and then expectorated. Subsequently a 0.02M aqueous solution of citric acid was taken. As a result, the citric acid solution showed an intense sweetness just like a sugar solution does.

This taste-modifier was introduced into a sterile Petri dish and allowed to stand at 37° C. for three months. Then it was subjected to the same sensory test as the one described above. As a result, it showed an intense sweetness similar to the above case.

EXAMPLE 3

100 l of water was added to 20 kg of *Curculigo latifolia* sarcocarp ground in the same manner as the one described in Example 1. Then the mixture was homogenized and centrifuged at 10,000 rpm for 30 minutes. After removing the supernatant, 100 l of water was added to the residue and the obtained mixture was homogenized and centrifuged, each in the same manner as the one described above, followed by removing the supernatant. To the obtained residue, was added 30 l of a 0.5M NaCl solution and the mixture was homogenized in a mixer for two minutes and then filtered under reduced pressure. After collecting the filtrate, 30 l of a 0.5M NaCl solution was further added to the residue. The mixture was homogenized and filtered under reduced pressure followed by collecting the filtrate.

These filtrates were combined and centrifuged at 30,000 rpm for one hour to thereby give a crude curuculin extract as the supernatant.

This crude extract was desalted by ultrafiltration and concentrated to a volume of 5 l. Then it was pasteurized with a VTIS pasteurizer (manufactured by Alfa-Laval) at 130° C. for five seconds. Then it was aseptically filled in a container to thereby give a taste-modifier in the form of an aqueous solution.

1 ml of this taste-modifier aqueous solution was kept in the mouth for a minutes and then expectorated. A 0.02M aqueous solution of citric acid, which was taken thereafter, tasted highly sweet just like a sugar solution does.

The container was allowed to stand as such for three months and then opened. Then the content was subjected to the same sensory test as the one described above. As a result, it tasted highly sweet similar to the above case.

COMPARATIVE EXAMPLE 1

*Curculigo latifolia* sarcocarp ground in the same manner as the one described in Example 1 was lyophilized to thereby give a taste-modifier.

Immediately after the preparation, this taste-modifier showed a taste-modification effect comparable to that of the taste-modifier of Example 1. After allowing to stand in a sterile Petri dish for three months at 37° C., however, it showed no sweetness but a sourness in the same sensory test as the one described above.

COMPARATIVE EXAMPLE 2

The procedure of Example 2 was repeated except that no heating was conducted to thereby give a taste-modifier.

This taste-modifier was allowed to stand in a sterile Petri dish for three months at 37° C. and then subjected to the same sensory test as the one described in Example 2. As a result, it showed a slight sweetness and an intense sourness.

What is claimed is:

1. A method for stabilizing a taste-modifier obtained from fresh *Curculigo latifolia* fruits or dried fruits thereof comprising extracting the fresh or dired *Curculigo latifolia* fruits with an aqueous salt solution comprising 0.01M to 1.0M of a chloride, phosphate, carbonate, sulfate, sulfite, nitrate, lactate, alum, burnt alum, sodium acetate, pyrophosphate, propionate, sodium benzoate, sodium fumarate or sodium polyacetate salt; and thereafter subjecting said taste-modifier to ultrahigh-temperature short-time pasteurization at 110° to 150° C. for two seconds to two minutes, without lowering the taste-modification activity of said taste-modifier.

2. The method of claim 3 wherein the salt is sodium chloride.

3. The method of claim 3 wherein the salt concentration is 0.1 to 1.0M.

4. The method of claim 3 wherein the extracting step comprises homogenizing a mixture of the salt solution and the *Curculigo latifolia* fruits; thereafter filtering and centrifuging the mixture to separate an extract from the extracted fruit; and thereafter, desalting the extract to produce the taste modifier.

* * * * *